US006638949B1

United States Patent
Folkman et al.

(12)

(10) Patent No.: US 6,638,949 B1
(45) Date of Patent: Oct. 28, 2003

(54) PREVENTION OF ADHESIONS AND EXCESSIVE SCAR FORMATION USING ANGIOGENESIS INHIBITORS

(76) Inventors: Judah Folkman, 18 Chatham Cir., Brookline, MA (US) 02146; Harold Brem, 300 E. 93$^{rd}$ St., Apt. 41C, New York, NY (US) 10128; H. Paul Ehrlich, 995 Jonestown Rd., P.O. Box 545, Grantville, PA (US) 17028

( * ) Notice: Subject to any disclaimer, the term of this patent is extended or adjusted under 35 U.S.C. 154(b) by 511 days.

(21) Appl. No.: 09/139,375

(22) Filed: Aug. 25, 1998

Related U.S. Application Data

(60) Provisional application No. 60/056,765, filed on Aug. 25, 1997.

(51) Int. Cl.$^7$ ............................................. A61K 31/445
(52) U.S. Cl. ........................................................ 514/323
(58) Field of Search .......................................... 514/323

(56) References Cited

U.S. PATENT DOCUMENTS

| | | | |
|---|---|---|---|
| 4,704,383 A | | 11/1987 | McNamara et al. ......... 514/152 |
| 4,900,815 A | * | 2/1990 | Tanaka et al. ................. 536/54 |
| 4,925,833 A | | 5/1990 | McNamara et al. ......... 514/152 |
| 4,935,411 A | | 6/1990 | McNamara et al. ......... 514/152 |
| 4,975,422 A | | 12/1990 | Kanoh et al. .................. 514/54 |
| 5,576,330 A | | 11/1996 | Buzzetti et al. .............. 514/307 |
| 5,605,684 A | * | 2/1997 | Piacquadio ............... 424/78.02 |
| 5,629,340 A | * | 5/1997 | Kuwano et al. ............. 514/461 |
| 5,670,493 A | | 9/1997 | Cordi et al. ................... 514/80 |
| 5,674,483 A | * | 10/1997 | Tu et al. |
| 5,712,291 A | | 1/1998 | D'Amato ..................... 514/323 |
| 5,792,845 A | | 8/1998 | O'Reilly et al. ............ 536/23.1 |

FOREIGN PATENT DOCUMENTS

| | | |
|---|---|---|
| EP | 0 325 199 | 1/1989 |
| EP | 325199 A2 * | 7/1989 |
| EP | 0 325 199 * | 7/1989 |
| WO | WO 95/04142 | 2/1995 |
| WO | WO 95/29242 A1 | 11/1995 |
| WO | WO 97/15666 | 5/1997 |

OTHER PUBLICATIONS

Arbiser, "Angiogenesis and the skin: A primer", J. Amer. Acad. Derm. 34(3):486–497 (1996).
Berman, et al., "Recurrence rates of excised keloids treated with postoperative triamcinolone acetonide injections or interferon alfa–2b injections," J. Am. Acad. Dermatol. 37: 755–757 (1997).
Berman, et al., "Keloids," J. Am. Acad. Dermatol. 33:117–123 (1995).
Bieley, et al., "Effects of a water–impermeable, non–silicon–based occlusive dressing on keloids," J. Am. Acad. Dermatol. 35: 113–114 (1996).
Brem, H., et al., "Brain tumor angiogenesis." In: Kornblith, et al.(eds.), Advances in Neuro–Oncology, pp. 89–101. (Future Publishing Co., Mount Kisco, NY (1988).

Brem, et al., "Inhibition of neovascularization by an extract derived from vitreous," Am. J. Ophthal. 84:323–328 (1977).
Brem and Folkman, "Inhibition of tumor angiogenesis mediated by cartilage," J. Exp. Med. 141: 427–439 (1975).
Brem, H., et al., "Inhibition of Tumor Angiogenesis by a Diffusible Factor from Cartilage," in Extracellular Matrices Influences on Gene Expression pp. 767–772 (Academic Press, NY 1975).
Cosman, et al., "Bilateral earlobe keloids," Plast. Reconstr. Surg. 53: 540–543 (1974).
Crum, R., et al., "A new class of steroids inhibits angiogenesis in the presence of heparin or a heparin fragment," Science 230: 1375–1378 (1985).
Darzi, et al., "Evaluation of various methods of treating keloids and hypertrophic scars: a 10–year follow–up study," Br. J. Plast. Surg. 45: 374–379 (1992).
Ehrlich, H.P., et al., "Morphological and immunochemical differences between keloid and hypertrophic scar," Am. J. Pathol. 145:105–113 (1994).
Ehrlich, et al., "Hypertrophic scar: an interruption in the remodeling of repair—a laser Doppler blood flow study," Plast. Reconstr. Surg. 90:993–998 (1992).
Eisentein, et al., Growth regulators in connective tissue. Systemic administration of an aortic extract inhibits tumor growth in mice, Am. J. Pathol. 9(1): 1–9 (1978).
Folkman, "Angiogenesis and its inhibitors," in Important Advances in Oncology DeVita, et al., eds., pp. 42–62, (J. B. Lippincott Co., Philadelphia, 1985).
Folkman, J. "Successful treatment of an angiogenic disease." N. Engl. J. Med., 320: 1211–1212 (1989).

(List continued on next page.)

Primary Examiner—Dwayne C. Jones
(74) Attorney, Agent, or Firm—Holland & Knight LLP

(57) ABSTRACT

A method and compositions for inhibiting excessive scar formation and adhesions by administering to a patient in need thereof an effective amount of an angiogenesis inhibitor. In the preferred embodiment, the angiogenesis inhibitor is selective, such as a fumagillol derivative like 0-chloroacetylcarbamoyl-Fumagillol (TNP-470, TAP Pharmaceuticals), thalidomide, or a selective drug having more than one activity, such as minocycline or penicilliamine which also have antibiotic activity. Less selective compounds can also be used, such as the cytokine IL12. Patients to be treated include those having experienced trauma, surgical intervention, burns, and other types of injuries. The inhibitor is administered in an amount effective to decrease excessive scarring, defined as formation of high density tissue including cells and connective tissue, without preventing normal wound closure. The inhibitors can be administered systemically and/or locally or topically, as needed. For prevention of adhesions, the angiogenesis inhibitor would typically be applied at the time of surgery, preferably in a controlled release formulation and/or using barrier technology.

21 Claims, 2 Drawing Sheets

OTHER PUBLICATIONS

Folkman, J. "Tumor angiogenesis: therapeutic implications," *N. Engl. J. Med.,* 285; 1182–1186 (1971).

Folkman, J., et al., "Angiogenesis inhibition and tumor regression caused by heparin or a heparin fragment in the presence of cortisone," *Science* 221: 719–725 (1983).

Folkman, J., et al., "Control of angiogenesis with synthetic heparin substitutes," *Science* 243: 1490–1493 (1989).

Fulton, "Silicone gel sheeting for the prevention and management of evolving hypertrophic and keloid scars," *Dermatol. Surg.* 21: 947–951 (1995).

Golub, L. M., et al., "A non–antibacterial chemically–modified tetracycline inhibits mammalian collagenase activity," *J. Dent. Res.,* 66: 1310–1314 (1987).

Golub, L. M., et al., "Further evidence that tetracyclines inhibit collagenase activity in human crevicular fluid and from other mammalian sources," *J. Periodontal Res.* 20: 12–23 (1985).

Golub, L. M., et al., "Tetracycline inhibit tissue collagenase activity. A new mechanism in the treatment of periodontal disease," *J. Periodontal Res.* 19: 651–655 (1984).

Golub, L. M., et al., "Minocycline reduces gingival collagenolytic activity during diabetes. Preliminary observations and a proposed new mechanism of action," *J. Periodontal Res.,* 18:516–526 (1983).

Griffith, et al., "A follow–up study on the treatment of keloids with triamicinolone acetonide," *Plast. Reconstr. Surg.* 46: 145–150 (1970).

Ingber, D., et al. "Inhibition of angiogenesis through modulation of collagen metabolism," *Lab. Invest.* 59: 44–51 (1989).

Ingber, D., et al., "Mechanochemical switching between growth and differentiation during fibroblast growth factor–stimulated angiogenesis in vitro: role of extracellular matrix," *J. Cell. Biol.* 109: 317–330 (1989).

Ingber, D., et al., "A Possible Mechanism for Inhibition of Angiogenesis by Angiostatic Steroids: Introduction of Capillary Basement Membrane Dissolution," *Endocrinol.* 119: 1768–1775 (1986).

Kessler, D.A., et al., "Mast cells and tumor angiogenesis," *Int. J. Cancer* 18:703–709 (1976).

Klumpar, et al., "Keloids treated with excision followed by radiation therapy," *J. Am. Acad. Dermatol.* 31: 225–231 (1994).

Langer, et al., "Control of tumor growth in animals by infusion of an angiogenesis inhibitor," *Proc. Natl. Acad. Sci. USA* 77: 4331–4335 (1980).

Langer, et al., "Isolation of a cartilage factor that inhibits tumor neovascularization," *Science* 193(4247): 70–72 (1976).

Larrabee, et al., "Intralesional interferon gamma treatment for keloids and hypertrophic scars," *Arch. Otolaryngol. Head Neck Surg.* 116: 1159–1162 (1990).

Lee, et al., "Shark cartilage contains inhibitors of tumor angiogenesis," *Science* 221: 1185–1187 (1983).

Martell, et al.,. "The 6–deoxytetracyclines. VII. Alkylated aminotetracyclines possessing unique antibacterial activity," *J . Med. Chem.,* 10: 44–46 (1967).

Murray, J. B., et al., "Purification and partial amino acid sequence of a bovine cartilage–derived collagenase inhibitor," *J. Biol. Chem.,* 261: 4154–4159 (1986).

Pauli, et al., "Regulation of tumor invasion by cartilage–derived anti–invasion factor in vitro," *J. Natl. Cancer Inst.* 67:65–73 (1981).

Rockwell, et al., "Keloids and hypertrophic scars: a comprehensive review," *Plast. Reconstr. Surg.* 827–835 (1989).

Zbinovsky, et al., "Minocycline," In: K. Florey (ed.), *Analytical Profiles of Drug Substances,* pp. 323–339 (Academic Press, NY 1977).

Arbiser, J. L., "Angiogenesis and the skin: A primer", J. Amer. Acad. Derm. 34(3):486–497, 1996.*

Fulton, J. E., "Silicone Gell Sheeting for the Prevention and Management of Evolving Hypertrophic and Keloid Scars", Dermatol. Surg. 21:947–951, 1995.*

* cited by examiner

PREVENTION OF ADHESIONS AND EXCESSIVE SCAR FORMATION USING ANGIOGENESIS INHIBITORS

This application claims priority to provisional application U.S. Ser. No. 60/056,765 entitled "Use of an Angiogenesis Inhibitor to Prevent Adhesions and Excessive Scar Formation" filed Aug. 25, 1997, by Judah Folkman and Harold Brem.

BACKGROUND OF THE INVENTION

The present invention relates to methods for the prevention of adhesions, excessive scar formation and other types of abnormal proliferation of tissue using angiogenesis inhibitors.

Scars are the result of wounds that have healed, lesions due to diseases, or surgical operations. Hypertrophic and keloid scars occur when the tissue response is out of proportion to the amount of scar tissue required for normal repair and healing. A keloid scar is a raised, firm, thickened red scar that exceeds the boundary of the injury and may grow for a prolonged period of time. The increase in scar size is due to deposition of all increased amount of collagen into the tissue. African-Americans are genetically prone to developing keloids. Keloid development has been associated with different types of skin injury including surgery, ear piercing, laceration, burns, vaccination or inflammatory process. Common sites are earlobes and the upper trunk and extremities. Surgical removal of keloids alone has been associated with a recurrence rate of 45% to 100%.

The problem of excessive scar formation that manifests itself clinically is a multi-billion dollar problem. For example, intra-abdominal adhesions results in a very significant morbidity and mortality in every surgery practice. Greater than 400,000 hospital admissions in the United States per year are for treatment of pelvic adhesions following surgery. Repeat surgery can greatly aggravate scarring.

There is no effective treatment to prevent adhesions, although numerous different technologies have been tried, including application of barriers which are designed to avoid direct tissue to tissue interactions, and administration of immunosuppressants to decrease inflammatory reactions. Currently there is only one product approved by the FDA for intra-abdominal and one product approved by the FDA for pelvic adhesions. These are principally mechanical barriers to adhesion formation. They are only minimally effective clinically and there remains a huge demand for an alternative. Keloids have been treated with injection of corticosteroid into the scar, by laser therapy, and by administration of pharmacologic agents that interfere with collagen synthesis. Numerous treatments after excision have been used, such as postexcisional injections of corticosteroids or interferon, silicone sheeting, radiotherapy, and pressure splints or garments. See, for example, Berman, et al., *J. Am. Acad. Dermatol.* 33, 117–123 (1995); Pulton, *Dermatol. Surg.* 21, 947–951 (1995); Cosman, et al., *Plast. Reconstr. Surg.* 53, 540–543 (1974); Rockwell, et al., *Plast. Reconstr. Surg.* 827–835 (1989); Griffin, et al., *Plast. Reconstr. Surg.* 46, 145–150 (1970); Bisley, et al., *J. Am. Acad. Dermatol.* 35, 113–114 (1996); Klumper, et al., *J. Acad. Dermatol.* 31, 225–231 (1994); Larrabee, et al., *Arch. Otolaryngol. Head Neck Surg.* 116, 1159–1162 (1990); Darzi, et al., *J. Plast. Surg.* 45, 374–379 (1992); and Berman, et al., *J. Am. Acad. Dermatol.* 37, 755–757 (1997).

It is therefore an object of the present invention to provide a treatment for prevention of excessive scarring and adhesions, without the inhibition of wound healing.

SUMMARY OF THE INVENTION

A method and compositions for inhibiting excessive scar formation and adhesions by administering to a patient in need thereof an effective amount of an angiogenesis inhibitor. In the preferred embodiment, the angiogenesis inhibitor is selective, such as a fumagillol derivative like 0-chloroacetylcarbamoyl-Fumagillol (TNP-470, TAP Pharmaceuticals), thalidomide, or a selective drug having more than one activity, such as minocycline or penicillamine which also have antibiotic activity. Less selective compounds can also be used, such as the cytokine IL12. Patients to be treated include those having experienced trauma, surgical intervention, burns, and other types of injuries. The inhibitor is administered in an amount effective to decrease excessive scarring, defined as formation of high density tissue including cells and connective tissue, without preventing normal wound closure. The inhibitors can be administered systemically and/or locally or topically, as needed. For prevention of adhesions, the angiogenesis inhibitor would typically be applied at the time of surgery, preferably in a controlled release formulation and/or using barrier technology.

DETAILED DESCRIPTION OF THE INVENTION

Figure 1:
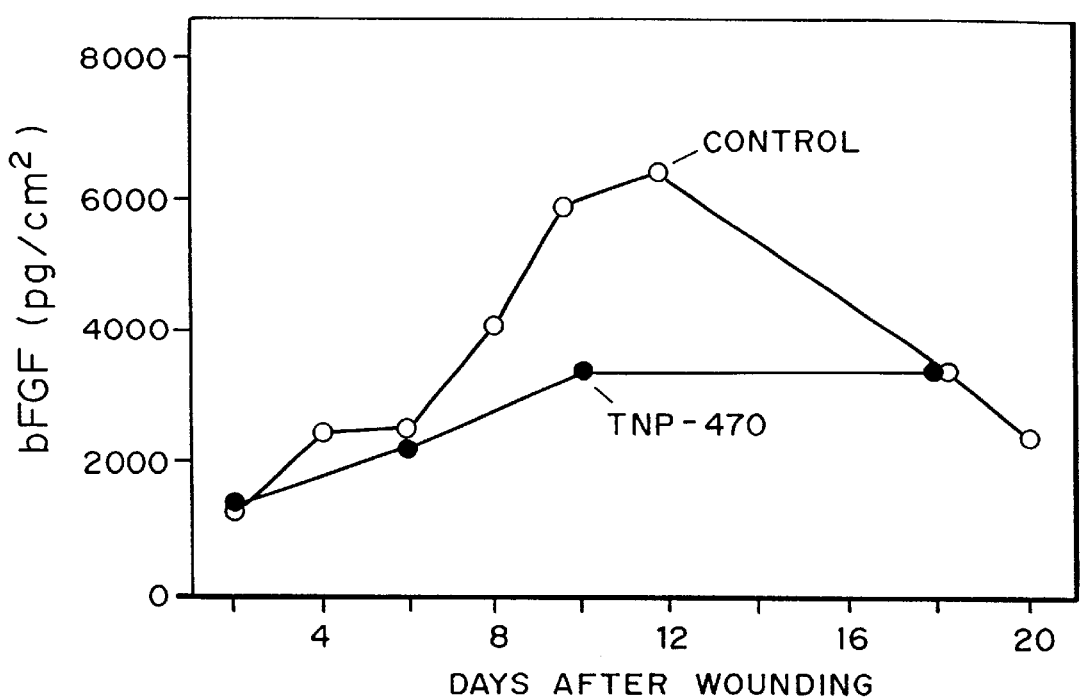
FIG. 1 is a graph of endogenous basic fibroblast growth factor (bFGF)(pg/cm2) over time (days after wounding) of mice treated with TNP-470 (solid circles) and controls that were not treated (open circles).

It has been discovered that excessive scar formation and adhesions can be prevented or inhibited by administration of an effective amount of anti-angiogenesis inhibitors.

Primate skin and soft tissue does not the regenerate. Instead function is restored by the deposition of new connective tissue, a scar. The extent of scarring is proportional to and related to the severity of tissue loss (in terms of volume and depth). Commonly, a deep wound involving a significant loss of dermis will heal with the deposition of excess scar, a hypertrophic scar. Another form of excess scarring which is much less common is the keloid scar. The keloid scar exceeds the boundaries of the original injury. Its intrusion into uninvolved surrounding skin differs from that of a hypertrophic scar which remains within the boundaries of the original injury. Another difference that distinguishes these abnormal scars is the presence of nodules in hypertrophic scars and their absence in keloids. Both abnormal scar conditions are characterized by the excess deposition of connective tissue, composed of a relatively high density of cells, and increased volume of connective tissue matrix and an increased vascular supply resulting from increased number of vessels. Evidence gathered by laser Doppler blood monitoring demonstrated that hypertrophic scars developed as a consequence of a defect in the remodeling phase of repair (Ehrlich, H. P., Kelley, S. F. (1992) *Plast. Reconstr.*

*Surg.* 90:993–998). No evidence was found that supported that the hypertrophic scar was the uninterrupted continuation of the proliferative phase of repair. Keloid scars also exhibit a high density of blood vessels and enhanced circulation within the connective tissue scar tissues (Ehrlich, H. P., et al. (1994) *Am. J. Pathol.* 145:105–113). Therefore, diminishing blood supply or preventing the development of an increased blood supply with a higher density of blood vessels, will block and retard the development of excess scarring.

Scar formation is the end product of the wound healing process. This process occurs as a series of overlapping phases that occur over a period of time. The initial phase called the lag phase is characterized by tile deposition of a transitional matrix mostly composed of fibrin and an inflammatory response. Following the lag phase, there is the proliferative phase of repair which is characterized by the invasion by and an increased density of mesenchymal cells, the syntheses and deposition of a new connective tissue matrix, the completion of re-epithelialization and the development of a new blood supply. The remodeling phase of repair terminates the proliferative phase and is characterized by a decrease in cell density, the better organization of the connective tissue matrix, and intact maturing epidermal surface and a decrease in the density of blood vessels. It is clear that without the reduction in blood vessel density, the remodeling phase of repair is impaired and an immature, excessive fibrotic tissue is deposited within the healed wound site. The nutritional requirement of the mesenchymal cells in excess scar tissue requires an enhanced blood supply. Preventing the development of that blood supply will block the development of excess scarring.

The control of angiogenesis represents the controls of the nutrient supply to the mesenchymal cells responsible for the synthesis and organization of the newly deposited connective tissue matrix of scar or fibrotic tissues. Without an adequate nutrient supply, limitations on the function and synthetic activity of mesenchymal cells occurs. Blocking the progression of angiogenesis will limit the nutrients supplied to mesenchymal cells and limit their metabolic activity.

I. Therapeutic Compositions
A. Anti-Angiogenesis Inhibitors

Angiogenesis, the proliferation and migration of endothelial cells that result in the formation of new blood vessels, is an essential event in a wide variety of normal and pathological processes. For example, angiogenesis plays a critical role in embryogenesis, wound healing, psoriasis, diabetic retinopathy, and tumor formation, as reported by Folkman, J. *Angiogenesis and its inhibitors.* In: V. T. DeVita, S. Hellman and S. A. Rosenberg (eds.). *Important Advances in Oncology*, pp. 42–62, (J. B. Lippincott Co., Philadelphia, 1985); Brem, H., et al., *Brain tumor angiogenesis.* In: P. L. Kornblith and M. D. Walker (eds.), *Advances in Neuro-Oncolocy.* pp. 89–101. (Future Publishing Co., Mount Kisco, N.Y. 1988); Folkmain. J. *Tumor angiogenesis: therapeutic implications. N. Engl. J. Med.*, 285: 1182–1186 (1971); and Folkman, J. *Successful treatment of an angiogenic disease. N. Engl. J. Med.*, 320: 1211–1212 (1989).

Identification of several agents that inhibit tumor angiogenesis has provided a conceptual framework for the understanding of angiogenesis in general. The inhibition of angiogenesis by certain steroids and heparin derivatives, reported by Folkman, J., et al., *Science* 221: 719 (1983); and Murray, J. B., et al., *Purification and partial amino acid sequence of a bovine cartilage-derived collagenase inhibitor. J. Biol. Chem.*, 261: 4154–4159 (1986); led to studies elucidating the crucial role of remodeling of the extracellular matrix in angiogenesis. These agents apparently prevent angiogenesis by specifically disrupting the deposition and cross-linking of collagen, as reported by Ingber, D., and Folkman, J. *Inhibition of angiogenesis through modulation of collagen metabolism. Lab. Invest.*, 59: 44–51 (1989).

The original description of angiogenesis inhibition in the presence of cartilage, reported by Brem, H., et al., *J. Exp. Med.* 141: 427–439 (1975); Brem, H., et al., *Extracellular Matrices Influences on Gene Expression* pp. 767–772 (Academic Press, N.Y. 1975); and Langer, R., et al., *Science* 70–72 (1976); led to the isolation and purification from bovine cartilage of a protein fraction that not only inhibited angiogenesis but inhibited protease activity, described by Murray, J. B., et al., *J. Biol. Chem.* 261: 4154–4159 (1986). Subsequently, an extract derived from the vitreous of rabbits was shown to inhibit tumor angiogenesis by Brem, S., et al., *Am. J. Ophthal.* 84: 323–328 (1977). The demonstration that heparin alone enhanced the angioenesis response buttressed the hypothesis that heparin produced by mast cells that had migrated to the tumor site facilitated the development of new capillaries, as reported by Kessler, D. A., et al., *Int. J. Cancer* 18:703–709 (1976).

Other studies on inhibition of angiogenesis have highlighted the importance of enzyme mediated remodeling of the extracellular matrix in capillary growth and proliferation (Folkman, J., et al., *Science* 221: 719–725 (1983); Ingber, D., et al. *Lab. Invest.* 59: 44–51 (1989); Folkman, J., et al., *Science* 243: 1490–1493 (1989); Krum, R., et al., *Science* 230: 1375–1378 (1985); Ingber, D., et al., *Endocrinol.* 119: 1768–1775 (1986): and Ingber, D., et al., *J. Cell. Biol.* 109: 317–330 (1989)). A number of investigators have reported that extracts of cartilage, one of the few avascular tissues in the body, can inhibit angiogenesis: Eisentein, et al., *Am. J. Pathol.* 81, 1–9 (1987); Pauli, et al., *J. Natl. Cancer Inst.* 67,55–74 (1981): Brent and Folkman, *J. Exp. Med.* 141, 427–439 (1975); Langer, et al., *Science* 193, 70–72 (1976); Langer, et al., *Proc. Natl. Acad. Sci. USA* 77, 431–435 (1980); and Lee and Langer, *Science* 221, 1185–1187 (1983).

Several different classes of compounds have been determined to be useful as inhibitors of angiogenesis. These incude collagenase inhibitors such as metalloproteinases and tetracyclines such as minocycline, fungal and bacterial derivatives, such as fumagillol derivatives like TNP-470, the sulfated polysaccharides described in U.S. Pat. No. 4,900,815 to Tanaka, et al. and the protein-polysaccharides of U.S. Pat. No. 4,975.422 to Kanoh, et al. and synthetic compounds such as the 2,5-diaryltetrahydrofurans of U.S. Pat. No. 5,629,340 to Kuwano, et al., aminophenylphosphonic acid compounds of U.S. Pat. No. 5,670,493 to Cordi, et al., the 3-substituted oxindole derivatives of U.S. Pat. No. 5,576, 330 to Buzzetti, et al., and thalidomides of U.S. Pat. No. 5,712,291 to D'Amato.

The antibiotics that are useful as angiogenesis inhibitors are those having collagenase inhibitory activity. These include the tetracyclines and chemically modified tetracyclines (CMTs), and three ringed tetracycline homologs, that have the ability to inhibit collagenase but diminished antibacterial activity. Examples of commercially available tetracyclines include chlotetracyline, demeclyeycline, doxycycline, lymecycline, methacycline, minocycline, oxytetracycline, rolitetracycline, and tetracycline. The active salts, which are formed through protonation of the dimethylamino group on carbon atom 4, exist as crystalline compounds. These are stabilized in aqueous solution by addition of acid.

Minocycline, a semisynthetic tetracycline antimicrobial, described by Martell, M. J., and Boothe, J. H. in *J. Med.*

*Chem.*, 10: 44–46 (1967), and Zbinovsky, Y., and Chrikian, G. P. *Minocycline*. In: K. Florey (ed.), *Analytical Profiles of Drug Substances*, pp. 323–339 (Academic Press, N.Y. 1977), the teachings of which are incorporated herein, has anticollagenase properties, as reported by Golub. L. M., et al., ,*J. Periodontal Res.*, 18: 516–526 (1983); Golub, L. M., et al.,*J. Periodontal Res.* 19: 651–655 (1984); Golub, L. M., et al., *J. Periodontal Res.* 20: 12–23 (1985); and Golub, L. M., et al.,*J. Dent. Res.*, 66: 1310–1314 (1987). Minocycline, first described in 1967, is derived from the naturally produced parent compounds chlortetracycline and oxytetracycline. The chemically modified tetracyclines are described by U.S. Pat. No. 4,704,383 to McNamara, et al., U.S. Pat. No. 4,925,833 to McNamara, et al., and U.S. Pat. No. 4,935,411 to McNamara, et al., the teachings of which are incorporated herein.

Other examplary anti-angiogenic compounds include penicillamine and some cytokines such as IL12.

B. Carriers

Pharmaceutical compositions containing the angiogenesis inhibitor are prepared based on the specific application. Application can be either topical, localized, or systemic. Any of these compositions may also include preservatives, antioxidants, antibiotics, immunosuppressants, and other biologically or pharmaceutically effective agents which do not exert a detrimental effect on the normal tissue to be treated.

Compositions for local or systemic administration will generally include an inert diluent. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

Systemic Carriers

Inhibitors can be systemically administered either parenterally or enterally. The composition can be administered by means of an infusion pump, for example, of the type used for delivering insulin or chemotherapy to specific organs or tumors, by injection, or by depo using a controlled or sustained release formulation. In a preferred systemic embodiment, drugs are administered orally, in an enteric carrier if necessary to protect the drug during passage through the stomach.

The angiogenic inhibitors can be administered systemically by injection in a carrier such as saline or phosphate buffered saline (PBS) or orally, in the case of an inhibitor such as thalidomide, in tablet or capsule form. The tablets or capsules can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch: a lubricant such as magnesium stearate or Sterotes; or a glidant such as colloidal silicon dioxide. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

Local or Topical Carriers

The angiogenic inhibitors can also be applied locally or topically, in a carrier such as saline or PBS, in an ointment or gel, in a transdermal patch or bandage, or controlled or sustained release formulation. Local administration can be by injection at the site of the injury, or by spraying topically onto the injury. The inhibitor can be absorbed into a bandage for direct application to the wound, or released from sutures or staples at the site. Incorporation of compounds into controlled or sustained release formulations is well known.

For topical application, the angiogenesis inhibitor is combined with a carrier so that an effective dosage is delivered, based on the desired activity, at the site of application. The topical composition can be applied to the skin for treatment of diseases such as psoriasis. The carrier may be in the form of an ointment, cream, gel, paste, foam, aerosol, suppository, pad or gelled stick. A topical composition for use of an ointment or gel consists of an effective amount of angiogenesis inhibitor in a ophthalmically acceptable excipient such as buffered saline, mineral oil, vegetable oils such as corn or arachis oil, petroleum jelly, Miglyol 182, alcohol solutions, or liposomes or liposome-like products.

In a preferred form for controlled release, the composition is administered in combination with a biocompatible polymeric implant which releases the angiogenesis.inhibitor over a controlled period of time at a selected site. Examples of preferred biodegradable polymeric materials include polyanhydrides, polyorthoesters, polyglycolic acid, polylactic acid, polyethylene vinyl acetate, and copolymers and blends thereof. Examples of preferred non-biodegradable polymeric materials include ethylene vinyl acetate copolymers. These can be prepared using standard techniques as microspheres, microcapsules, tablets, disks, sheets, and fibers.

C. Other Therapeutic Agents which can be Administered in Combination

The angiogenic inhibitors can be administered alone or in combination with other treatments. For example, the inhibitors can be administered with antibiotics, cytokines, and antiinflammatories such as cortisone, and/or other types of angiogenic inhibitors. Other combinations will be apparent to those skilled in the art. In a preferred embodiment for prevention of adhesions, the angiogenesis inhibitor is administered with a barrier, such as methylcellulose or other polymeric material, either topically at the time of surgery or incorporated into the barrier, which is inserted at the time of surgery. In some cases the combination therapy will be achieved through the selection of the angiogenesis inhibitor, for example, minocycline, which both inhibits collagenase and is an antibiotic. One of the causes of the failure of intestinal anastamosis is the breakdown of connective tissue by enhanced collagenase activity. The inhibition of this collagenase activity may be beneficial or improve the outcome of these surgical procedures.

II. Methods of Treatment

A. Disorders to be Treated

The angiogenic inhibitors can be used to prevent or inhibit excessive scar formation, especially hypertrophic scars and keloid scars, and adhesions, especially intra-peritoneal or pelvic adhesions such as those resulting after open or laproscopic surgery, and burn contractions. Other conditions which should be beneficially treated using the angiogenesis inhibitors include prevention of scarring following transplantation, cirrhosis of the liver, pulmonary fibrosis following acute respiratory distress syndrom or other pulmonary fibrosis of the newborn, implantation of temporary prosthetics, and adhesions after surgery between the brain and the dura.

B. Effective Dosages and Treatment Regimes

The angiogenesis inhibitor will typically be administered either at the time of surgery or shortly thereafter, usually within one week, except in those cases where the injury is to the skin or other superficial surface and can be readily accessed following the injury or surgery. A particular example of the latter is in the treatment of wounds. It is desirable to treat exposed wounds of the skin after there has been re-epithelialization of the skin's surface wounds in normal healthy patients may close in as short as five to several days; in deep burn patients wounds may take three to six weeks to close. Since the remodeling phase of repair occurs after the wound is closed, and there is a new epidermal surface preventing new growth of blood vessel as this is not detrimental to the healing process and will reduce normal skin-like barrier function no more than that of a normal scar. In the case of adhesions, the deposition of connective tissue between normal anatomical structures is unnecessary. Hence preventing the development of an enhanced blood supply to that tissue would not be detrimental to the host. On the other hand, preventing the closure of an open wound could he detrimental to the host. Therefore the time of commencement of therapy would be different in preventing adhesions and preventing excess dermal scarring. In the case of adhesions, therapy will start early, that is, soon after procedures which lead to local trauma and the deposition of a transitional matrix. On the other hand, with skin injury, the healing process would continue and therapy would be withheld until the wound was closed, as demonstrated by an intact epidermal surface.

The angiogenesis inhibitor is administered in a dosage and in a regimen that does not prevent wound healing, but does decrease the amount of blood vessel growth at the wound site to prevent or decrease formation of high density cellular and connective tissue within the scar or outside of the wound area (keloids). In order to have increased levels of cells and deposited connective tissue one must have an increased nutritionial supply viti vascularization. Dosages will typically be in the same range as used for inhibition of tumor growth, but administered to a different class of patients and for different time periods, since wound healing typically occurs over a much shorter time. Moreover, when administered topically or in a sustained release formulation, the dosage may be lower in order not to prevent wound healing.

The present invention will be further understood by reference to the following non-limiting examples.

EXAMPLE 1

Inhibition of Scar Formation

TNP-470 interferes with blood vessel and collagen formation resulting in decreased adhesions. As demonstrated by the following data, TNP-470 results in the abolishment of intra-abdominal adhesions.

Methods

Full thickness mouse wounds were made in adult mice, the majority of whom were six to eight weeks old and some of whom were fourteen to sixteen weeks old. Mice were pretreated for sixty days with TNP-470, then wounds were made, and healing monitored. Mice were treated with 30 mg/kg TNP-470 administered subcutaneously every other day.

Histological micrographs of open mouse wounds harvested at 7, 12, and 17 days post excision were made. The biopsies were fixed, embedded, sectioned and stained with hematoxylin and eosin.

Results

Examination of 7-day untreated healing wound granulation tissue showed a high density of blood vessels with some large patent vessels.

Examination of 7-day TNP-470 treated healing wound granulation tissue showed a relatively lower density of blood vessels, with some having smaller patent vessels.

Examination of a 12-day untreated closed wound showed granulation tissue under a re-epithelialized surface with numerous patent blood vessels.

Examination of a 12-day TNP-470 treated healing wound that is not completely closed, showed that granulation tissue under a re-epithelialized surface shows fewer vessels with smaller diameters.

Examination of a 17-day untreated healed wound showed mature granulation tissue with patent vessels, but a reduced density of mesenchymal cells.

Examination of a 17-day TNP-470 treated healed wound showed mature granulation tissue with a reduction in the number of vessels, but a continued higher density of mesenchymal cells.

The histologic findings demonstrate that TNP-470 severely retarded scar formation. At 7 days the treatment group had a lower density of blood vessels and reduced granulation tissue compared to untreated controls. In contrast, mesenchymal cell infiltration was similar in treated compared to untreated animals. At 12 days the open wounds in the controls were completely re-epithelialized and revealed a greater density of patent vessels, compared to partially closed TNP 470-treated wound. In addition, the density of mesenchymal cells in the TNP-470 treated granulation tissue appeared greater than in the controls and the epidermal surface was thicker in the treated group. At 17 days, when both treated and untreated mouse wounds were closed, the density of blood vessels remained elevated in the untreated mice, compared to the treated mice which had a lower density of blood vessels. In contrast, at day 17 after wounding, the density of mesenchymal cells and the thickness of the epidermis was greater in TNP470 treated mice. Thicker epidermis and greater density of mesenchymal cells represent retarded scar maturation. Thus inhibition of angiogenesis by TNP-470 resulted in retarded wound closure by wound contraction and re-epithelialization and also increased time required for maturation of granulation tissue.

EXAMPLE 2

Inhibition of Scarring During Wound Healing

Further experiments were conducted to examine the role of the angiogenic inhibitors in wound healing and prevention of excessive scarring.

Methods

Mice were treated essentially the same as described in Example 1.

Results

As demonstrated by FIG. 1, endogenous synthesis of basic fibroblast growth factor in the wound is decreased after treatment with the angiogenesis inhibitor, TNP-470. Treatment of mice with the angiogenesis inhibitor TNP-470 resulted in an average of 37% reduction of bFGF concentration on day 10 after wound ($p \leq 0.05$). This data suggests that one possible mechanism of TNP-470's ability to inhibit angiogenesis is as a consequence of the decreased amount of basic fibroblast growth factor in the wound.

Histological analysis of the wounds in the control and treated mice compared contraction of full thickness wounds in mice treated with systemic TNP-470 (AGM 1470), every other day after the wound is made, with untreated mice. Treatment with TNP-470 every other day after the wound is made (at a dose identical to that which results in maximal tumor inhibition) causes a 5-day delay in the complete contraction of the wound.

Figure 2:
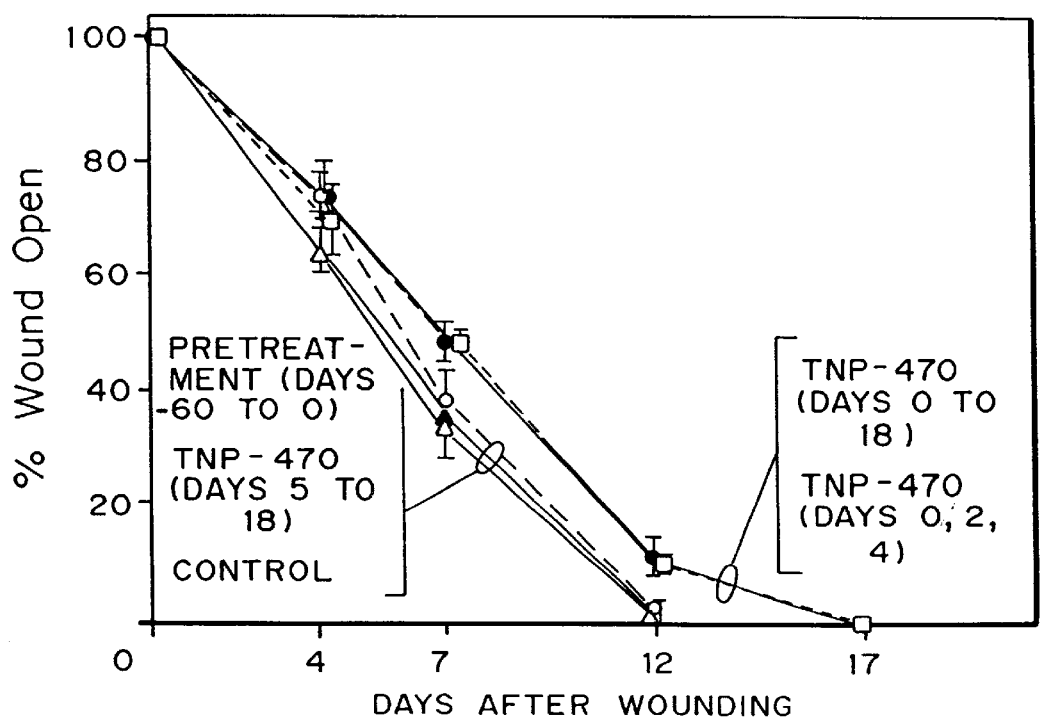
FIG. 2 is a graph of percent wounds open over time (days after wounding) for mice treated with TNP-470 for different dosage regimes: pretreatment days −60 to day 0; treated with TNP-470 days 5 to 18; treated with TNP-470 days 0 to 18; and treated with TNP-470 days 0, 2 and 4.

FIG. 2 (n=440 mice) compares wound closure following different treatment regimes. TNP-470 inhibited or slowed wound healing by 5 days to full contraction. This was statistically significant. The wound healing remained inhibited if TNP-470 was given on post wound days 0, 2, 4, or post wound days 0, 2, 4, 6, 8, and 10.

Figure 3:
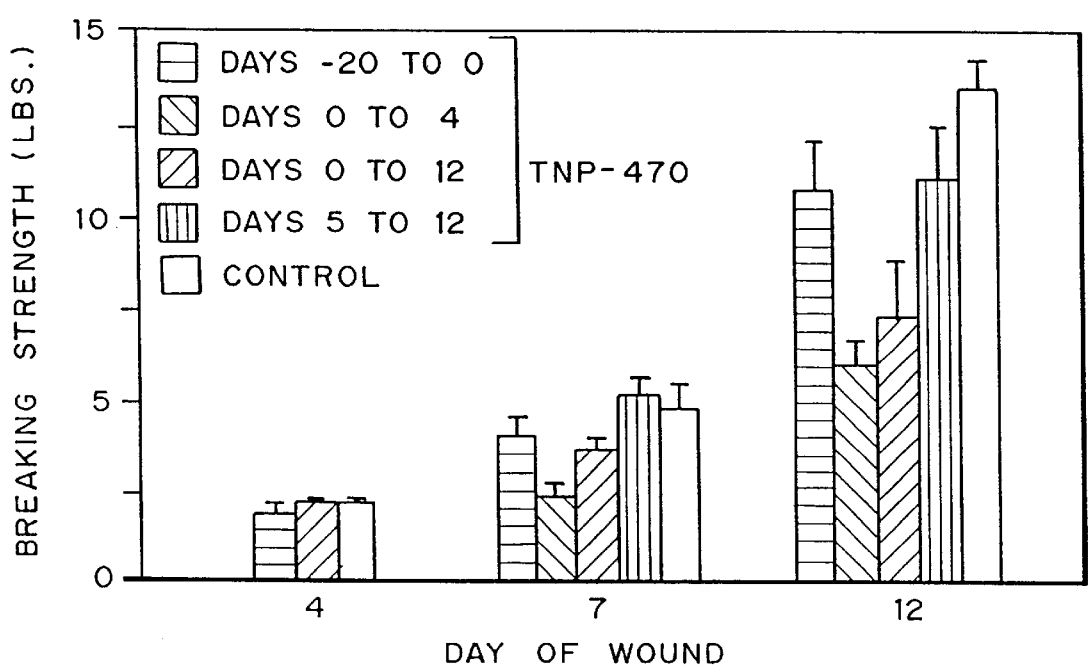
FIG. 3 is a graph of breaking strength (tensile strength) of linear wounds after systemic administration of TNP-470 days −20 to 0; days 0 to 4; days 0 to 12; days 5 to 12; and control, measured on days 4, 7 and 12 after wounding.

FIG. 3 (n=280 mice)graphs breaking strength of linear wounds after systemic administration of TNP-470. Breaking strength was inhibited 36% on post wound day 7 and 43% on post wound day 12. This was statistically significant. The wounds were inhibited if TNP-470 was given on post wound days 0, 2, 4 or post wound days 0, 2, 4, 6, 8, and 10.

Modifications and variations of the present invention will be obvious to those skilled in the art from the foregoing detailed description. Such modifications and variations are intended to come within the scope of the appended claims.

We claim:

1. A method to inhibit excessive scar formation and adhesions comprising administering to a patient in need thereof an effective amount of an angiogenesis inhibitor selected from the group consisting of collagenase inhibitors, penicillamine, and IL12.

2. The method of claim 1 wherein the angiogenesis inhibitor is administered systemically.

3. The method of claim 1 wherein the angiogenesis inhibitor is administered topically or locally at the site of a wound.

4. The method of claim 1 wherein the angiogenesis inhibitor is administered to prevent or inhibit formation of hypertrophic scarring.

5. The method of claim 1 wherein the angiogenesis inhibitor is administered to prevent or inhibit formation of keloid scarring.

6. A method for inhibiting surgical adhesions or burn contractions comprising administering to the site an effective amount of angiogenesis inhibitor selected from the group comprising thalidomide, collagenase inhibitors, penicillamine, and IL12.

7. The method of claim 1 wherein the angiogenesis inhibitor is an antibiotic.

8. The method of claim 6 wherein the angiogenesis inhibitor is thalidomide.

9. A method for inhibiting surgical adhesions or burn contractions comprising administering to the site an effective amount of fumigillin in a pharmaceutically acceptable topical carrier selected from the group consisting of an ointment, gel spray, and paste, for application to a wound.

10. A composition for application to a wound comprising a polymeric barrier or implant comprising an angiogenesis inhibitor selected from the group comprising thalidomide, fumigillin, collagenase inhibitors, and penicillamine, in a dosage formulation comprising a pharmaceutically acceptable carrier for topical application in an amount effective to prevent or inhibit formation of hypertrophic scars or keloid scars, adhesions or burn contractions.

11. A composition comprising an angiogenesis inhibitor selected from the group consisting of collagenase inhibitors and penicillamine, in a pharmaceutically acceptable carrier for topical application of the inhibitor selected from the group consisting of an ointment, gel, spray, and paste.

12. The composition of claim 10 wherein the angiogenesis inhibitor is thalidomide.

13. The composition of claim 10 wherein the angiogenesis inhibitor is in a controlled release formulation which releases an effective amount of angiogenesis inhibitor to prevent or inhibit hypertrophic scar or keloid scar formation over the time period required for healing of a wound.

14. The composition of claim 10 wherein the angiogenesis inhibitor is in a formulation delivering sustained release of an effective amount of angiogenesis inhibitor to prevent or inhibit hypertrophic scar or keloid scar formation over the time period required for healing of a wound.

15. The composition of claim 10 in a dosage not inhibiting normal wound healing.

16. The method of claim 1 wherein the angiogenesis inhibitor is a collagenase inhibitor.

17. The method of claim 1 wherein the angiogenesis inhibitor is penicillamine.

18. The method of claim 1 wherein the angiogenesis inhibitor is IL12.

19. The method of claim 6 wherein the angiogenesis inhibitor is a collagenase inhibitor.

20. The method of claim 6 wherein the angiogenesis inhibitor is penicillamine.

21. The method of claim 6 wherein the angiogenesis inhibitor is IL12.

* * * * *